United States Patent [19]

Cook et al.

[11] Patent Number: 4,495,150
[45] Date of Patent: Jan. 22, 1985

[54] MULTIPLE OBJECT CAPTURING AND PROCESSING DEVICE

[75] Inventors: William E. Cook, Vista; Morton A. Vodian, Escondido; Otto Haunold, Carlsbad, all of Calif.

[73] Assignee: Beckman Instruments, Inc., Fullerton, Calif.

[21] Appl. No.: 516,486

[22] Filed: Jul. 25, 1983

[51] Int. Cl.³ .................. B01L 9/00; B01D 35/02; B08B 3/00
[52] U.S. Cl. .................. 422/99; 422/104; 422/71; 211/74; 134/115 R
[58] Field of Search .......... 422/99, 101, 102, 104, 422/71; 211/74; 73/863.82, 423 R; 134/115 R; 436/809, 807; 273/1 R, 1 G, 1 GG

[56] References Cited

U.S. PATENT DOCUMENTS

| | | |
|---|---|---|
| 2,729,363 | 1/1956 | Bauer et al. |
| 3,154,225 | 10/1964 | Wadlinger et al. |
| 3,250,283 | 5/1966 | Reinfeld |
| 3,342,375 | 9/1967 | Johnson et al. |
| 3,488,052 | 1/1970 | Weisbecker ................. 273/1 R |
| 3,564,256 | 2/1971 | Arkman et al. |
| 3,932,141 | 1/1976 | Beall et al. |
| 3,949,771 | 4/1976 | Dodge et al. |
| 4,034,884 | 7/1977 | White |
| 4,038,149 | 7/1977 | Liner et al. |
| 4,065,383 | 12/1977 | Skare et al. |
| 4,090,850 | 5/1978 | Chen et al. |
| 4,146,365 | 3/1979 | Kay et al. |
| 4,154,795 | 5/1979 | Thorne |
| 4,198,020 | 4/1980 | Walker et al. ................. 248/499 |
| 4,200,613 | 4/1980 | Alfrey et al. |
| 4,284,603 | 8/1981 | Korom |
| 4,320,087 | 3/1982 | Chau et al. |

FOREIGN PATENT DOCUMENTS

| | | | |
|---|---|---|---|
| 493773 | 6/1953 | Canada ................. 422/102 |
| 2404466 | 1/1979 | France |
| 197808 | 8/1978 | United Kingdom ........ 422/102 |

Primary Examiner—Arnold Turk
Assistant Examiner—Joseph P. Carrier
Attorney, Agent, or Firm—W. H. May; J. E. Vanderburgh; R. S. Frieman

[57] ABSTRACT

A device for handling and washing beads. The device is attachable to a test tube rack and includes a frame, a containing slide, and a capture slide. By manipulating the slides in various combinations of positions the beads may be added to, removed from, or separately washed apart from test tubes in the rack. Complete and easy washing of the beads may thus be accomplished.

9 Claims, 7 Drawing Figures

MULTIPLE OBJECT CAPTURING AND PROCESSING DEVICE

BACKGROUND OF THE INVENTION

1. Field of the Invention

The invention is directed to a manipulative laboratory device. More particularly, the invention is a laboratory apparatus which includes means for separating a constituent. In still greater particularity, the invention is an apparatus for retaining and washing a plurality of objects. By way of further characterization, but not by way of limitation thereto, the invention is a device which is attachable to a test tube rack and in which a plurality of beads may be contained and washed after having been separated from the test tubes.

2. Description of the Prior Art

In an immunochemical assay, an object such as a plastic bead is coated with an immuno reactant such as an antibody or antigen. The bead is added to a sample containing the complementary antibody or antigen to be assayed. If present, the immuno reactant in the sample will react with the affixed immuno reactant and thereby adhere to the bead. A reagent containing a known quantity of one of the immuno reactants which has been labeled with a detectable member such as an enzyme, radioisotope or fluorescent moiety can then be added to react with one of the reactants on the bead. The bead can then be separated from the reaction medium and examined to determine the presence or absence of labeled reagent.

The separation of the bead from the reaction medium can be accomplished in a number of ways. One method involves aspirating the liquid phase from the reaction vessel. Another method involves carefully decanting the liquid, and still another involves using a reaction container with a crimped or constricted orifice to retain the object while allowing the liquid phase to be poured off.

A method and apparatus for washing beads in test tubes is disclosed in U.S. Pat. No. 4,284,603 issued on Aug. 18, 1981 to G. K. Korom. The device disclosed therein includes a test tube rack for vertically aligning a plurality of test tubes which can contain the bead and liquid phase of the reaction. The tops of the test tubes are covered with a porous retaining means. This retaining means keeps the test tubes in the rack and the beads in the test tubes. The retaining means is held in place by side portions which engage the sides of the test tube rack. The entire apparatus may be inverted and the liquid contents may be removed from the tubes while retaining the objects within the tubes. This apparatus allows liquid to be poured off from the test tube while retaining the solid object, or bead, within the test tubes.

While suitable for its intended purpose, the above described device uses a restrictive screen over the open end of the test tubes to retain the beads in the tubes. The device thereby produces slow water flow requiring vigorous shaking of the inverted rack to remove the washing liquid from the tubes. A number of washing cycles may be required in order to completely wash the beads within the tubes. In addition, because the test tubes are preferably disposed of after washing, this device unnecessarily requires the washing of test tubes which is not necessary. The device is thus cumbersome, difficult, and time comsuming to use, and requires repeated washing cycles to completely wash the beads.

SUMMARY OF THE INVENTION

The invention is a laboratory apparatus which includes a retaining means for retaining test tubes in a test tube rack. A capture slide and a containing slide are attached to the retaining means such that a bead may be added to, or removed from, the test tube for washing or other purposes. More specifically, the capture slide and the containing slide include holes which are sized to allow the beads to pass therethrough. The capture slide and the containing slide are each independently movable to a first position and a second position.

There are three combinations of slide positions which are useful in handling the beads for washing and evaluation purposes. That is, when the capture slide and the containing slide are in their respective first positions, beads may be added to the retaining means without dropping into the test tubes. When the capture slide is moved to a second position while the containing slide is maintained in the first position, the beads are allowed to drop into the test tubes but are prevented from falling out of the retaining means by the container slide. In this position, and upon completion of the reaction, the device may be inverted with the bead falling into the retaining means in contact with the container slide. In the inverted position, the capture slide and the container slide are simultaneously moved such that the containing slide is in a second position while the capture slide is in a first position. The bead is then held in the retaining means by the cooperation of the containing slide and the retaining means. The bead is, however, movable within that confined space to allow for complete and thorough washing.

DESCRIPTION OF THE PREFERRED EMBODIMENT

Figure 1:
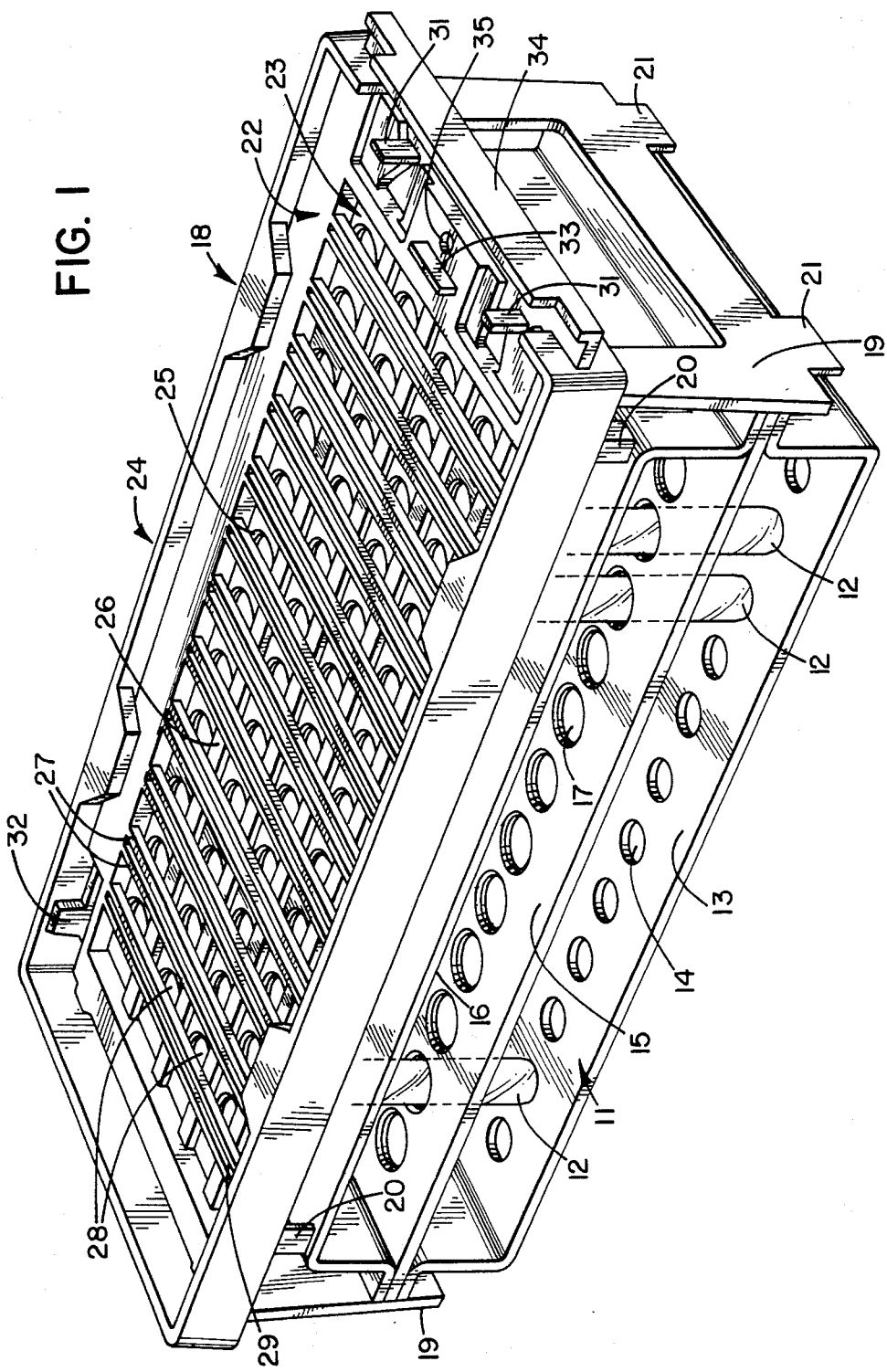
FIG. 1 is a perspective view of the device.

Referring to FIG. 1, a test tube rack 11 is adapted to receive a plurality of test tubes 12. Test tubes 12 are vertically aligned by three levels of test tube rack 11. That is, a lower level 13 includes a plurality of recesses 14 for receiving the lower portion of test tubes 12. Upper levels 15 and 16 of test tube rack 11 include hole 17 to maintain test tubes 12 in a vertical position.

A test processor generally designated as 18 is removably attached to test tube rack 11 by flexible wings 19. Spacers 20 are attached to processor 18 at each corner and rest on upper level 16 so that processor 18 does not contact test tubes 12. Thus, it is possible to attach processor 18 to rack 11 with less than a full complement of test tubes in rack 11 while still maintaining the stability of processor 18 on rack 11.

Tabs 21 on wings 19 serve to orient the test processor 18 on the test tube rack 11. That is, tabs 21 on each side of processor 18 are spaced different distances apart such that processor 18 can only be oriented onto rack 11 in one direction. Test processor 18 includes a containing slide 22 and a capture slide 23. Test processor 18 also includes a frame 24 for receiving containing slide 22 and capture slide 23. Frame 24 includes a plurality of holes (not shown) in alignment with the open ends of test tubes 12. The holes in frame 24 are sized to allow a bead to pass therethrough and into test tubes 12 but are smaller than the ends of test tubes 12 to prevent test tubes 12 from passing through frame 24 when the apparatus is inverted. Capture slide 23 includes holes 25 which are sized to allow a bead (not shown) to pass therethrough. Capture slide 23 is slidably mounted in frame 24 such that holes 25 are alignable with the holes in frame 24 in order that a bead may pass through capture slide 23 and frame 24 and thereby drop into a test tube 12.

Containing slide 22 includes a plurality of bars 26 which run the length of containing slide 22. Containing slide 22 also includes a plurality of ribs 27 extending the width of containing slide 22. Ribs 27 are arranged in pairs with a small distance between a rib and its adjacent rib comprising the pair and a larger distance between adjacent pairs of ribs 27. The distance from each pair of ribs 27 to each adjacent pair of ribs is wide enough to allow a bead to pass therethrough. However, the distance between each individual rib in the pair from its adjacent rib is small enough to prevent the bead from passing between the individual ribs comprising the pair. Similarly, bars 26 are spaced from the ends of retaining slide 22 and from each other a sufficient distance to allow beads to pass therethrough. The effect is that beads can pass through spaces designated as 28 but cannot pass through spaces designated as 29.

Containing slide 22 and capture slide 23 are movable with respect to frame 24. Containing slide 22 is movable by actuation of containing slide latches 31 and pulling of a containing slide handle 33. Capture slide 23 is movable upon actuation of capture slide latch 32 and pulling of a capture slide handle 34. A disassembly latch hole 35 may be used to separate containing slide 22 and capture slide 23 from frame 24 for cleaning or other purposes.

Figure 2:
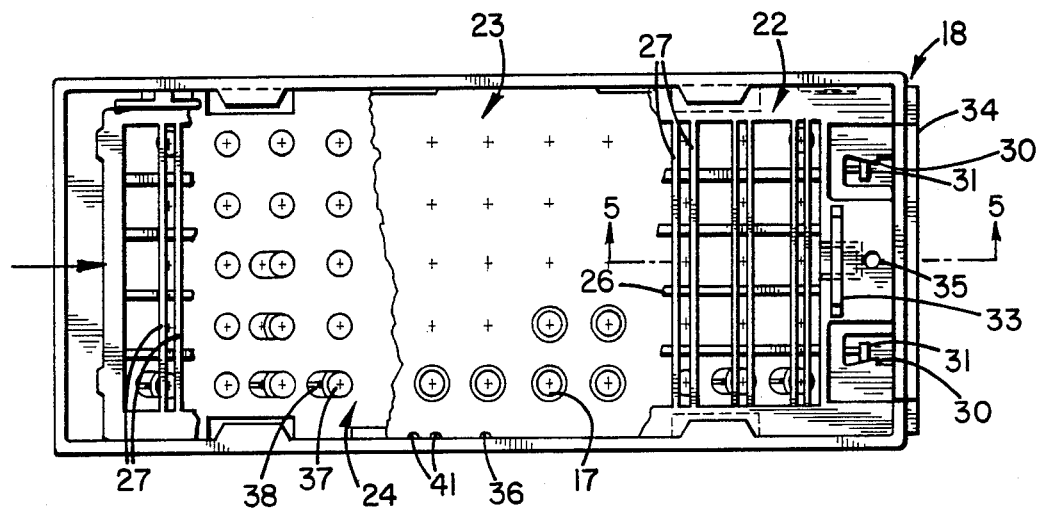
FIG. 2 is a top view of the retaining means.

Referring to FIG. 2, a top, partially cut away view of test processor 18 is shown. Frame 24 includes detents 36 mating with grooves 41 on capture slide 23 for positive positioning of capture slide 23 in its first and second positions. Bars 26 and ribs 27 on containing slide 22 are shown. Holes 25 in capture slide 23 are shown. Holes 37 and a wash area 38 in frame 24 are also shown.

Figure 3:
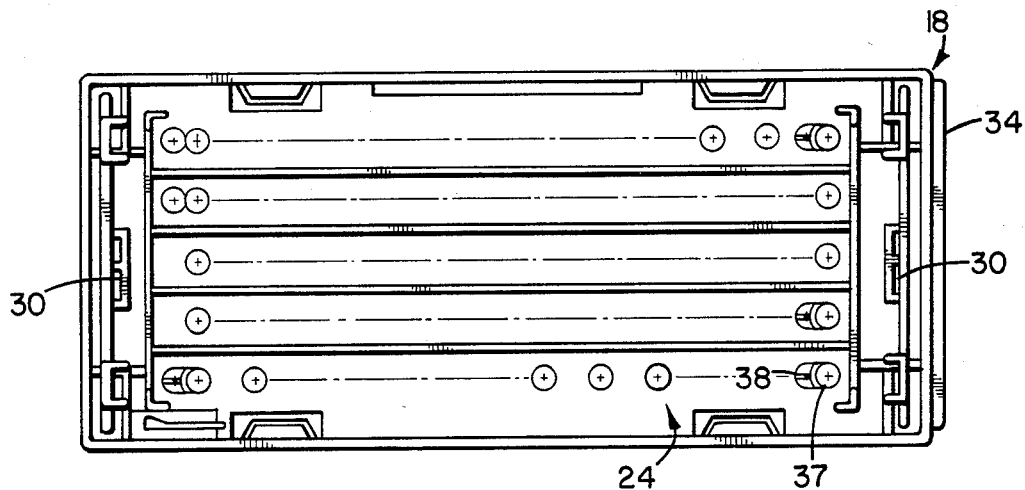
FIG. 3 is a bottom view of the retaining means.

Referring to FIG. 3, a bottom view of test processor 18 is shown. Frame 24 includes holes 37 which are sized the same as holes 25 to allow a bead to pass therethrough. Adjacent to each hole 37 is a wash area 38 which is an area designed to allow liquids to pass therethrough while not allowing beads to pass through.

Figure 4:
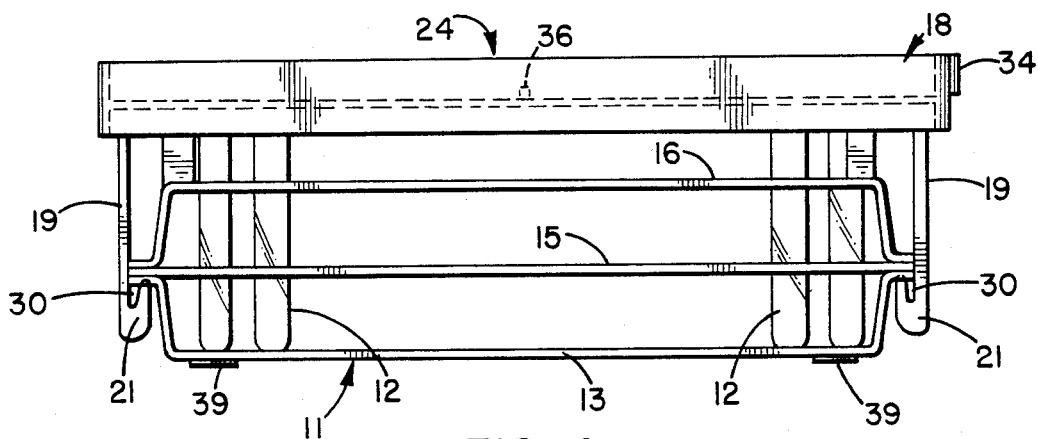
FIG. 4 is side view of the retaining means attached to the test tube rack.

Referring to FIG. 4, test tube rack 11 is shown with test processor 18 attached thereto by latches 30. Test tubes 12 are vertically aligned in test tube rack 11. A plurality of non-skid devices 39 are attached to the lower portion of test tube rack 11. Tabs 21 on the inside of wings 19, slide through grooves (not shown) on test tube rack 11 to orient processor 18 on rack 11.

Figure 5:
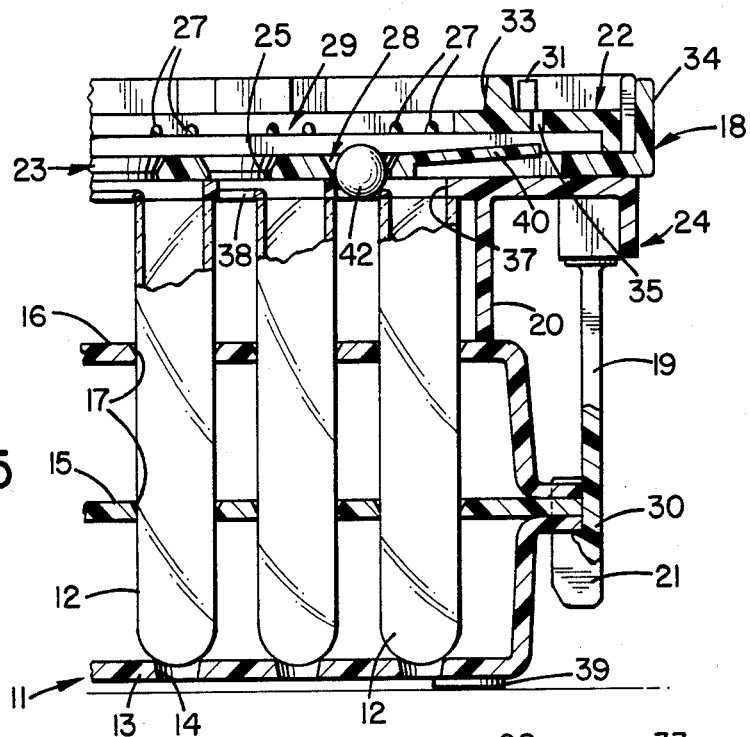
FIG. 5 is a partial side sectional view taken along the line 5—5 in FIG. 3.

Referring to FIG. 5, a partial side sectional view of test processor 18 is shown. Test tubes 12 are vertically aligned in test tube rack 11. Containing slide 22 and capture slide 23 are shown. Holes 37 in frame 24 allow beads 42 to drop into test tube 12. Similarly, holes 25 in capture slide 23 allow beads 42 to drop therethrough.

Also, spaces 28 defined by adjacent pairs of ribs 27 and containing slide 22 allow beads 42 to pass therethrough. However, the space 29 between individual ribs 27 will not allow beads 42 to pass therethrough. Similarly, wash area 38 will not allow beads 42 to pass therethrough. A disassembly latch 40 may be depressed through hole 35 to allow the apparatus to be disassembled. In FIG. 5 containing slide 22 and capture slide 23 are shown in their first positions.

Figure 6:
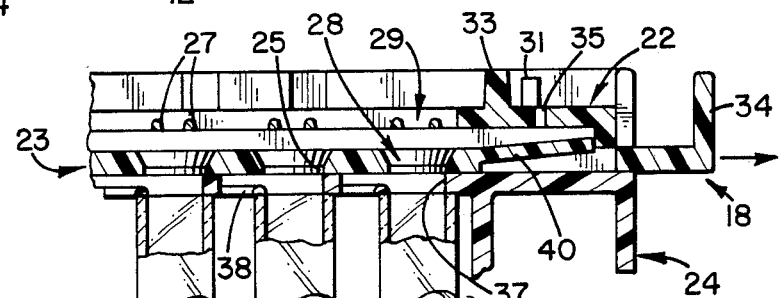
FIG. 6 is a partial side sectional view as in FIG. 4 with the capture slide in a second position.

Referring to FIG. 6, capture slide 23 has been moved to a second position while containing slide 22 is maintained in a first position. This allows beads 42 to drop into test tubes 12. That is, beads 42 pass through holes 25 in capture slide 23 and through holes 37 in frame 24 and into test tubes 12 by the force of gravity.

Figure 7:
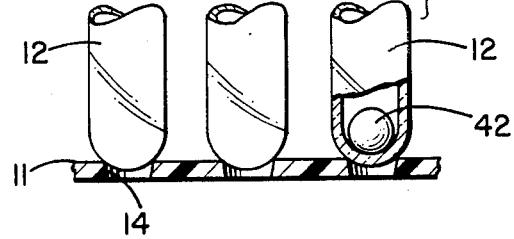
FIG. 7 is a partial side sectional view as in FIGS. 4 and 5 with the capture slide in a first position and the containing slide in a second position.

Referring to FIG. 7, capture slide 23 is in a first position while containing slide 22 is in a second position. In this arrangement, beads 42 are contained between ribs 27 and wash area 38. Beads 42 are thus effectively trapped in holes 25 and cannot fall out of test processor 18.

MODE OF OPERATION

In order to accomplish the immunoassay, test tubes 12 are placed in test tube rack 11. Test processor 18 is then latched to test tube rack 11 by latch 30 on wings 19. Test processor tabs 21 cooperate with grooves in rack 11 to orient the test processor 18 onto rack 11 in only one way thus insuring that the beads will be matched with their respective test tubes each time the test processor 18 is latched to, or removed from, test tube rack 11.

Referring to FIG. 5, once the test tubes 12 and test processor 18 have been placed in and on test tube rack 11, then the addition of beads 42 is accomplished with containing slide 22 and capture slide 23 in their respective first positions. Specifically, beads 42 are individually placed through spaces 28 and into holes 25 by the operator and come to rest against wash area 38.

Once the beads 42 have been placed in the test processor 18, capture slide latch 32 is depressed and capture slide 23 is moved to its second position as shown in FIG. 6. Containing slide 22 is prevented from moving into its second position by frame 24 which will not allow slide 22 to move beyond the boundary wall of frame 24. Disassembly latch 40 on capture slide 23 cooperates with lip 43 on containing slide 22 to prevent capture slide 23 from traveling beyond its second position. Thus, beads 42 drop into test tubes 12. Test processor 18 may then be removed from test tube rack 11 by moving test tube rack latches outward and lifting test processor 18 from test tube rack 11. The immunoassay may then be performed on the beads in each test tube.

During the immunoassay, as discussed above, it is necessary to wash the beads to remove unbound components of the assay. To perform this function, test processor 18 is latched to test tube rack 11 as described above. As noted previously, there is only one way to orient test processor 18 such that subsequent removal of beads from the test tubes and addition thereto will insure that each bead remains with the same test tube. Prior to washing, the operator insures that the test processor 18 is oriented as in FIG. 6. That is, containing slide 22 is in a first position and capture slide 23 is in a second position as shown in FIG. 6. At this point the entire unit is inverted allowing beads 42 to drop into holes 25 in capture slide 23. Beads 42 are prevented from falling out of the unit by ribs 27 in containing slide 22. The beads cannot pass through spaces 29 between ribs 27. While still in the inverted position, capture slide 23 is moved to the position shown in FIG. 7. That is, capture slide 23 is returned to the first position. Simultaneously, containing slide 22 is moved to a second position as shown in FIG. 7. This simultaneous movement of capture slide 23 and containing slide 22 is accomplished by latches 31 on capture slide 23. That is, latches 31 cooperate with notches 30 to move containing slide 22 into its second position when capture slide 23 is moved to its first position. When capture slide 23 is in its second position containing slide 22 is locked into its first position by frame 24, latches 31 and disassembly latch 40. This prevents loss of beads when the rack is inverted.

In the position shown in FIG. 7, beads 42 are trapped in the test processor 18. Test processor 18 may then be removed from the test tube rack 11. At this point, washing liquid may be directed over beads 42 either through wash area 38 or through space 29 between ribs 27. Thus, beads 42 may be washed independently of test tubes 12 without the time consuming and tedious procedures of continually filling and draining test tubes 12. In addition, beads 42 may be thoroughly rinsed and all remaining liquid removed therefrom without the necessity of vigorous shaking as in the prior art device. It is even possible that beads 42 may be dried if such is desired.

Once the beads are washed the immunoassay may continue. That is, beads 42 may be transferred to clean, dry test tubes for further immunoassay procedures. This is accomplished by attaching test processor 18 to a test tube rack 11. Containing slide 22 is moved to its first position such that beads 42 drop into test tubes 12 as is shown in FIG. 6. Test processor 18 may then be removed from the test tube rack 11 and the assay may continue.

Test processor 18 may be disassembled for cleaning and inspection. In order to accomplish this, capture slide 23 is moved to the second position while containing slide 22 is kept in its first position by frame 24. A probe is inserted in disassembly latch hole 35 and latch 40 (not shown) is depressed. Capture slide 23 is then pulled to the right and it will then separate from containing slide 24. Containing slide 22 may then be removed from frame 24. The unit may then be cleaned. To re-assemble, the containing slide 22 is inserted into frame 24 and capture slide 23 is then inserted between containing slide 22 and frame 24 until grooves 41 click into detent 36 in frame 24.

Use of test processor 18 allows beads 42 to be removed from test tubes 12 and washed separately. This type of washing allows the beads to be washed without the need to wash test tubes 12 which are disposed of after each use. In addition, the beads 42 can be washed more completely when separated from the test tubes. An even flow of liquid may be directed around each bead to uniformly wash the bead. Depending on the desire of the user, the test tubes may be washed or disposed of and fresh test tubes may be inserted. Because of tabs 21, test processor 18 may be attached to test tube rack 11 in only one position. Thus, there will be no mix-up of beads with respect to test tube positions. Slides 22 and 23 are locked to each other and to frame 24 by latches 31 and 32 when slide 23 is in its first position and slide 22 is in its second position as in FIG. 7. Thus, once the beads are captures and processor 18 is separated from rack 11 the beads cannot be inadvertently separated from processor 18. It would require positive action by the operator to depress latches 31 or 32 in order to move the slides and drop the beads.

The device allows for easily and completely washing the beads in an immunoassay procedure Ribs 27 prevent the beads from falling out of processor 18 and yet allow washing fluid to be directed onto beads 42 in the processor. It is also possible to dip the entire processor into washing fluid to wash the beads. While prior art devices have employed screens and the like held over test tubes, beads are washed within the test tubes and vigorous shaking is required to remove remaining liquid from the tubes. The present device eliminates the necessity for such time consuming and haphazard washing procedures. The present device allows beads to be completely and easily washed apart from the test tubes thus eliminating the unneeded step of washing the test tubes.

While particular forms of the invention have been disclosed with respect to a preferred embodiment thereof, it is not to be so limited in that modifications may be made which are within the full intended scope of the invention as defined by the appended claims. The description contained herein allows one skilled in the art to make and use a novel and unobvious device for the handling and washing of beads in an immunoassay procedure.

What is claimed is:

1. In a testing apparatus employing a plurality of test tubes with at least one solid object insertable into each test tube, said apparatus including a rack for maintaining said test tubes in vertical alignment and a means for retaining said test tubes in said rack when said rack is inverted, the improvement comprising:

said retaining means including means defining a first plurality of holes in alignment with said test tubes, said first holes sized to allow said objects to pass through said retaining means;

a capture slide movably mounted adjacent said retaining means, said capture slide including means defining a second plurality of holes to allow said object to pass therethrough, said capture slide movable to a first position in which said second holes in said capture slide are not in alignment with said first holes in said retaining means and a second position in which said second holes in said capture slide are in alignment with said first holes in said retaining means;

a containing slide, movably mounted adjacent said capture slide, said containing slide including means defining a first plurality of spaces to allow said object to pass therethrough, said containing slide movable to a first position in which said first spaces in said containing slide are not in alignment with said first holes in said retaining means and a second position in which said first spaces in said containing slide are in alignment with said first holes in said retaining means; and whereby, when said capture slide is in said first position and said containing slide is in said second position, then said object is contained in said retaining means by the cooperation of said containing slide and said retaining means.

2. Apparatus according to claim 1 wherein said retaining means includes a wash area adjacent each of said first holes in said retaining means, said wash area configured such that said objects cannot pass therethrough.

3. Apparatus according to claim 1 wherein said retaining means further includes means, cooperative with said test tube rack, for orienting said retaining means on said test tube rack.

4. Apparatus according to claim 1 wherein said retaining means further includes a latch for attaching said retaining means to said test tube rack.

5. Apparatus according to claim 1 wherein said retaining means includes means, connected to said retaining means, for spacing said retaining means from said test tube rack.

6. Apparatus according to claim 1 wherein said test tube rack further includes means, on the bottom of said test tube rack, for preventing said test tube rack from moving on a surface upon which it is placed.

7. Apparatus according to claim 1 further including means, associated with said capture slide and said containing slide for latching said capture slide and containing slide in predetermined positions.

8. Apparatus according to claim 1 wherein said containing slide includes means defining a second plurality of spaces sized so as to prevent said object from passing therethrough but sufficient to allow a washing liquid to pass therethrough.

9. Apparatus according to claim 8 wherein said second spaces are defined by a plurality of ribs arranged in pairs.

* * * * *